United States Patent
Xu et al.

(10) Patent No.: US 6,675,271 B1
(45) Date of Patent: Jan. 6, 2004

(54) PACS ARCHIVE TECHNIQUES

(75) Inventors: Xiaofeng Xu, Des Plaines, IL (US); Glenn Robert Kulpinski, Tinley Park, IL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/464,246

(22) Filed: Dec. 16, 1999

(51) Int. Cl.[7] ............................................. G06F 12/00
(52) U.S. Cl. ........................ 711/161; 711/114; 711/162; 711/170; 711/172; 705/2; 705/3; 600/300; 600/425
(58) Field of Search ............................... 711/114, 115, 711/117, 161–162; 707/200, 204; 705/2, 3; 379/106.02; 600/300, 425; 345/555; 709/247; 710/68

(56) References Cited

U.S. PATENT DOCUMENTS

| | | | |
|---|---|---|---|
| 4,652,999 A | | 3/1987 | Higashi et al. |
| 5,235,510 A | * | 8/1993 | Yamada et al. .............. 600/300 |
| 5,276,867 A | * | 1/1994 | Kenley et al. .............. 395/600 |
| 5,446,861 A | * | 8/1995 | Idleman et al. ............. 711/100 |
| 5,586,262 A | * | 12/1996 | Komatsu et al. ................ 705/2 |
| 5,619,995 A | * | 4/1997 | Lobodzinski ................. 348/77 |
| 5,751,997 A | * | 5/1998 | Kullick et al. .............. 709/215 |
| 5,829,046 A | * | 10/1998 | Tzelnic et al. .............. 711/100 |
| 5,867,821 A | * | 2/1999 | Ballantyne et al. ............ 705/2 |
| 6,104,859 A | * | 8/2000 | Yoshida et al. ............... 386/80 |
| 6,349,373 B2 | * | 2/2002 | Sitka et al. .................. 711/161 |
| 6,353,878 B1 | * | 3/2002 | Dunham ....................... 707/10 |
| 6,370,630 B1 | * | 4/2002 | Mizuyabu et al. .......... 711/167 |

FOREIGN PATENT DOCUMENTS

| | | | | |
|---|---|---|---|---|
| JP | 407141498 A | * | 6/1995 | ............ H04N/5/76 |

OTHER PUBLICATIONS

*PACS Basic Principles and Applications*, H.K. Huang, (A. John Wiley & Sons Publication 1999): "Picture Archiving and Communication System Components and Industrial Standards", Ch. 7, pp. 177–198A.

*PACS Basic Principles and Applications*, H.K. Huang (A. John Wiley & Sons Publication 1999): "Image Acquisition Gateway", Ch. 8, pp. 199–231;A. John Wiley & Sons Publication 1999.

*PACS Basic Principles and Applications*, H.K. Huang (A. John Wiley & Sons Publication 1999): "Display Workstation", Ch. 12, pp. 305–342.

http://www.fujindt.com/medical/; Fujifilm, Medical Imaging—Computed Radiography; author unknown, date unknown, printed on Nov. 18, 1999. Html pages: cr_process1; cr_process2; html pp: cr_process1; cr_process2; cr_process3; cr_process4; cr_process5; cr_process6; cr_basics; cr_whyfuji; advance; cr_synapse; crvsder; cr_application; cr_reference.

* cited by examiner

*Primary Examiner*—Matthew Kim
*Assistant Examiner*—Zhuo H. Li
(74) *Attorney, Agent, or Firm*—McAndrews, Held & Malloy, Ltd.; Peter J. Vogel; Michael A. Dellap una

(57) ABSTRACT

A PACS including a source of medical data, such as a CT unit (20), a workstation (100) capable of creating an image of the data, and a local area network (40). A server (60) stores compressed medical data in a RAID (70) and also in a magneto-optical unit (80) and a tape DLT unit (90). The tape unit (90) has a transfer rate equal to or greater than the transfer rate of the RAID.

21 Claims, 1 Drawing Sheet

PACS ARCHIVE TECHNIQUES

BACKGROUND OF THE INVENTION

This invention relates to picture archive and communication systems (PACS), and more specifically relates to archiving data in such systems.

Archive storage in PACS systems is provided for backing up images and other data once the data is not necessary at a short-term storage site. The archives are not redundant and there is a possibility that large quantities of information may be lost in the event of failure or servicing of the archive. This invention addresses the problem and provides one solution.

BRIEF SUMMARY OF THE INVENTION

The preferred embodiment of the invention is useful in a picture archive and communication system for archiving medical data. In such an environment, the preferred embodiment typically includes a source of medical data, a network, a first memory and a second memory. Data is received from the source of medical data, preferably over the network, and is stored, preferably in the first memory. The data then is transferred from the first memory to the second memory, preferably via the network, before the capacity of the first memory is exceeded. At some time, the stored data is transferred from the first memory or the second memory to the workstation to create an image.

By using the foregoing techniques, security can be provided for image data and other medical data. The data can be quickly and conveniently restored in the event of a failure, during servicing and during archive or medium replacement.

DETAILED DESCRIPTION OF THE INVENTION

Figure 1:
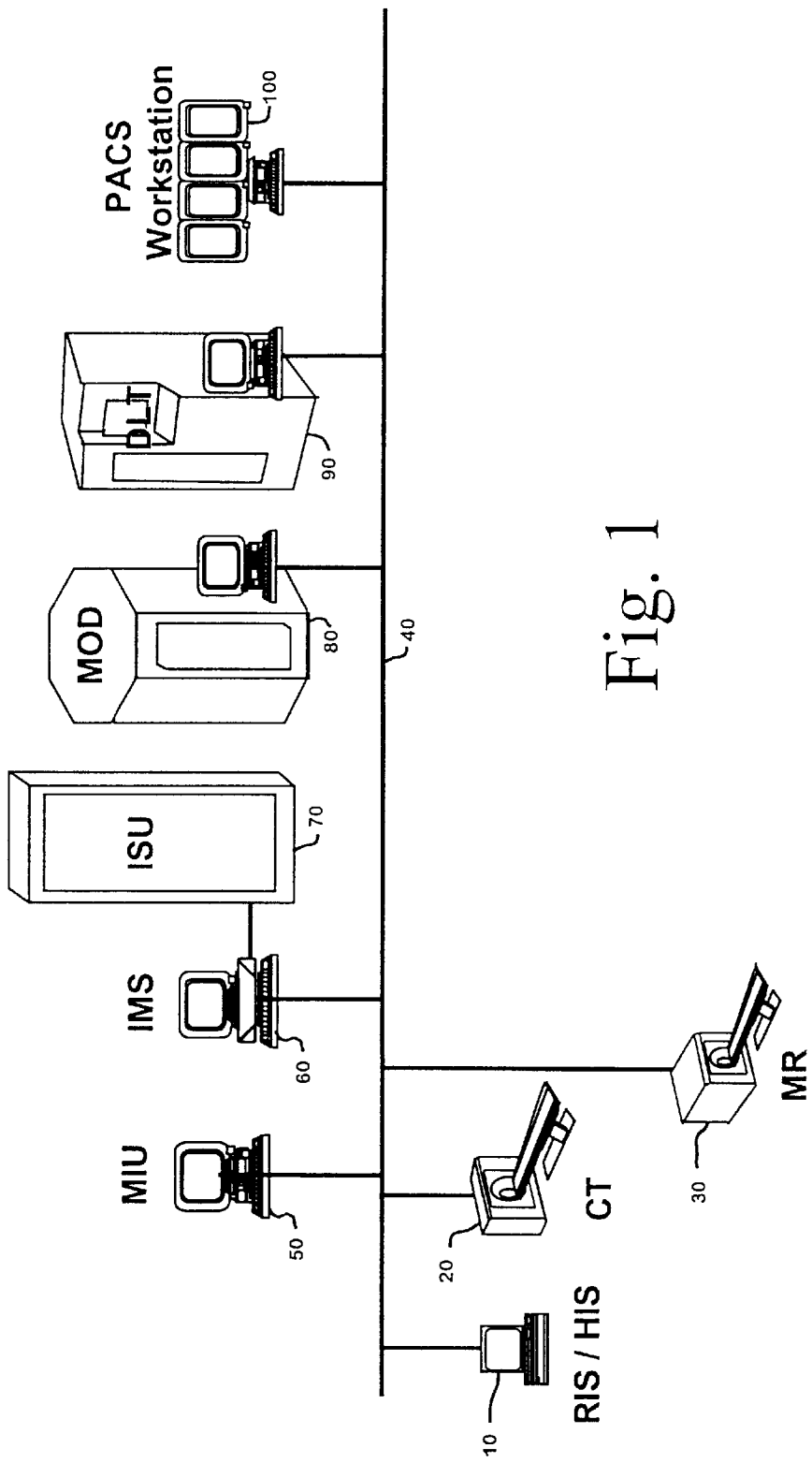
FIG. 1 is a schematic block diagram of a preferred form of the invention.

Referring to FIG. 1, a preferred form of the invention includes a radiology information system (RISIHIS) 10 which provides image data derived from x-rays of patients. A computed tomography (CT) unit 20 provides image data derived from scans of patients, and a magnetic resonance (MR) unit 30 provides image data from additional scans of patients. System 10 and units 20 and 30 also may provide text data about the image data generated by the respective units or about the circumstances of the patients or procedures from which the image data was derived. For example, the system and units may provide the name of the patient, the date of the creation of the image data, and various control numbers assigned to the procedures or image data.

The image data and text data are transmitted over a conventional local area network 40 to a modality interface unit (MIU) 50 in a well known manner. One example of MIU 50 is model number 2223612 made by General Electric Company.

Unit 50 compresses the image data in a well known manner and provides the compressed data, as well as the text data, to an information management server (IMS) 60 via network 40. One example of IMS 60 is model number 2244014 made by General Electric Company. The text data is stored in a data base in IMS 60. The compressed image data is transferred by IMS 60 to a short-term memory image storage unit (ISU) 70 which may comprise a RAID unit. RAID units are well known in PACS and need not be described in detail. Although ISU 70 is able to rapidly store data and access such data, its storage capacity is limited. As a result, data stored in ISU 70 frequently is read from ISU 70 by IMS 60 and is transferred via network 40 to a magneto-optical disk (MOD) memory unit 80. MOD 80 may be arranged as a jukebox managing, for example, 500 disks, each with a capacity of at least 5 gigabytes. Data may be written to and read from MOD memory 80 at a rate of at least 4 megabytes per second, and preferably 5 megabytes per second. One example of MOD 80 is model M-500 made by Plasmon.

In order to provide improved archiving of compressed image data, a digital logic tape (DLT) memory unit 90 is connected to network 40 as shown. DLT 90 provides a tape drive which moves a tape medium on which compressed image data is stored. DLT 90 has a storage capacity of at least 20 gigabytes and preferably 40 gigabytes. Data is written to and read from DLT 90 at a rate of at least 6 megabytes per second and preferably 10 megabytes per second. Examples of DLT 90 include model DLT 7000 made by Quantum and model 9840 made by StorageTek.

During use, at frequent intervals, IMS 60 reads data from ISU 70 and writes the data to DLT 90 via network 40. As a result, DLT 90 has a data transfer rate at least equal to the data transfer rate of ISU 70. The ability of DLT 90 to write data read directly from ISU 70 at the same rate as data is written to ISU 90 is an advantage because it reduces the risk that some data will be lost. The applicants have found that employing a tape unit, such as DLT 90, for this purpose also has cost advantages. Tape units are generally less expensive than RAIDs or magneto-optical units of the same capacity. By providing a tape unit with a data transfer rate as great as the data transfer rate of the ISU enables data to be archived with a degree of safety and economy not previously obtainable. Another advantage of the described system is the use a single server, IMS 60, to handle data transfers among ISU 70, MOD 80 and DLT 90. This arrangement enables a single operating system to be employed which improves software efficiency and reduces costs.

The preferred embodiment also includes conventional medical workstations 100 which create a viewable image on a monitor in response to image data received from any of ISU 70, MOD 80 or DLT 90. In response to a request by a user, IMS 60 accesses the desired data on one of ISU 70, MOD 80 or DLT 90, decompresses the data, and transfers the decompressed data via network 40 to a designated one of workstations 100.

Those skilled in the art will recognize the preceding is merely a description of the preferred embodiments which may be altered and modified without departing from the true spirit and scope of the invention as defined in the accompanying claims.

What is claimed is:

1. In a picture archive and communication system comprising a network, apparatus providing communication across said network comprising:

at least one source of medical data, connected to a network, to generate image data and corresponding text data;

a first memory, connected to said network, to receive said image data at a first data rate, and to store said image data;

a second memory, connected to said network, to receive said image data from said first memory at a second data rate before a first capacity of said first memory is exceeded; and an information management server for storing said corresponding text data and transferring said image data through said information management server from said first memory to said second memory at said second data rate, wherein said second data rate is higher than said first data rate; and at least one workstation, connected to said network, to receive said image data and said corresponding text data from said information management server to generate and display an image.

2. Apparatus, as claimed in claim 1, wherein the source of medical data comprises a computed tomography unit.

3. Apparatus, as claimed in claim 1, wherein the source of medical data comprises a magnetic resonance imaging unit.

4. Apparatus, as claimed in claim 1, wherein the network comprises a local area network.

5. Apparatus, as claimed in claim 1, wherein the workstation comprises a monitor.

6. Apparatus, as claimed in claim 1, wherein said first memory comprises a RAID.

7. Apparatus, as claimed in claim 1, wherein said first memory comprises a magneto optical storage unit capable of reading and writing data.

8. Apparatus, as claimed in claim 7, wherein said first memory can read data at a rate of at least 4 megabytes per second.

9. Apparatus, as claimed in claim 1, wherein said second memory comprises a tape storage unit.

10. Apparatus, as claimed in claim 9, wherein said second memory has a storage capacity of at least 20 gigabytes.

11. Apparatus, as claimed in claim 10, wherein said second memory has a transfer rate of at least 6 megabytes per second.

12. Apparatus, as claimed in claim 11, wherein said second memory has a transfer rate of at least 10 megabytes per second.

13. In a picture archive and communication system comprising a network, a method of archiving medical data comprising:

generating medical image data and corresponding text data;

transferring said image data and said corresponding text data over said network;

storing said image data in a first memory on said network at a first data rate;

storing said corresponding text data within an information management server for storing said corresponding text data and transferring said image data through said information management server from said first memory to a second memory at a second data rate, wherein said second data rate is higher than said first data rate;

transferring said image data from said first memory to a second memory through said information management server;

retrieving said image data from said first memory or said second memory over said network; and transferring said image data and said corresponding text data over said network for display.

14. A method, as claimed in claim 13, wherein said generating medical image data comprises imaging a patient by computed tomography.

15. A method, as claimed in claim 13, wherein said generating medical image data comprises magnetic resonance imaging.

16. A method, as claimed in claim 13, wherein said storing said image data in said first memory comprises storing said image data at a rate of at least 4 megabytes per second.

17. A method, as claimed in claim 13, wherein said transferring said image data to said second memory comprises moving a tape medium.

18. A method, as claimed in claim 17, wherein said transferring said image data to said second memory comprises providing at least 20 gigabytes of storage.

19. A method, as claimed in claim 18, wherein said transferring said image data to said second memory comprises transferring said image data at a rate of at least 6 megabytes per second.

20. A method, as claimed in claim 18, wherein said transferring said image data to said second memory comprises transferring said image data at a rate of at least 10 megabytes per second.

21. A system for archiving medical data comprising:

a source of medical data including image data and corresponding text data;

a first memory for receiving and storing said image data at a first data rate;

a second memory for receiving and storing said image data at a second data rate; and an information management server for storing said corresponding text data and transferring said image data through said information management server from said first memory to said second memory at said second data rate, wherein said second data rate is higher than said first data rate.

\* \* \* \* \*